United States Patent [19]

Danby et al.

[11] Patent Number: 4,559,045
[45] Date of Patent: Dec. 17, 1985

[54] PINCH VALVE ASSEMBLY

[75] Inventors: Hal C. Danby, Palo Alto; Carl Ritson, San Jose, both of Calif.

[73] Assignee: Anatros Corporation, San Jose, Calif.

[21] Appl. No.: 493,182

[22] Filed: May 10, 1983

[51] Int. Cl.[4] ............................................. A61M 5/00
[52] U.S. Cl. ...................................... 604/250; 604/34; 604/245; 251/7
[58] Field of Search ................. 604/250, 34, 245, 246; 251/7, 8, 9, 133

[56] References Cited

U.S. PATENT DOCUMENTS

| 3,831,625 | 8/1974 | Roediger | 604/250 X |
| 3,915,167 | 10/1975 | Waterman | 604/250 |
| 4,300,552 | 11/1981 | Cannon | 604/250 X |
| 4,312,493 | 1/1982 | Stauffer | 604/250 X |
| 4,337,791 | 7/1982 | Tech et al. | 251/8 X |
| 4,398,908 | 8/1983 | Siposs | 604/250 X |

Primary Examiner—Stephen C. Pellegrino
Attorney, Agent, or Firm—William B. Walker

[57] ABSTRACT

A disposable pinch valve assembly for parenteral solution delivery systems comprises a two-piece tubing receptor housing hingedly connected and with an irreversible snap connection which will not permit removal of the device from parenteral tubing after assembly. A back section has an integral movable pressure plate attached to the housing by integral flexible web connectors. When the movable plate is actuated toward the stationary press surface, tubing is pinched therebetween and the cross-section area of the flow passage through the tubing is reduced. The movable pressure plate is designed to engage a actuator connector which engages the device with a motor-driven actuator in an axially sliding engagement.

7 Claims, 14 Drawing Figures

U.S. Patent   Dec. 17, 1985   Sheet 1 of 3   4,559,045
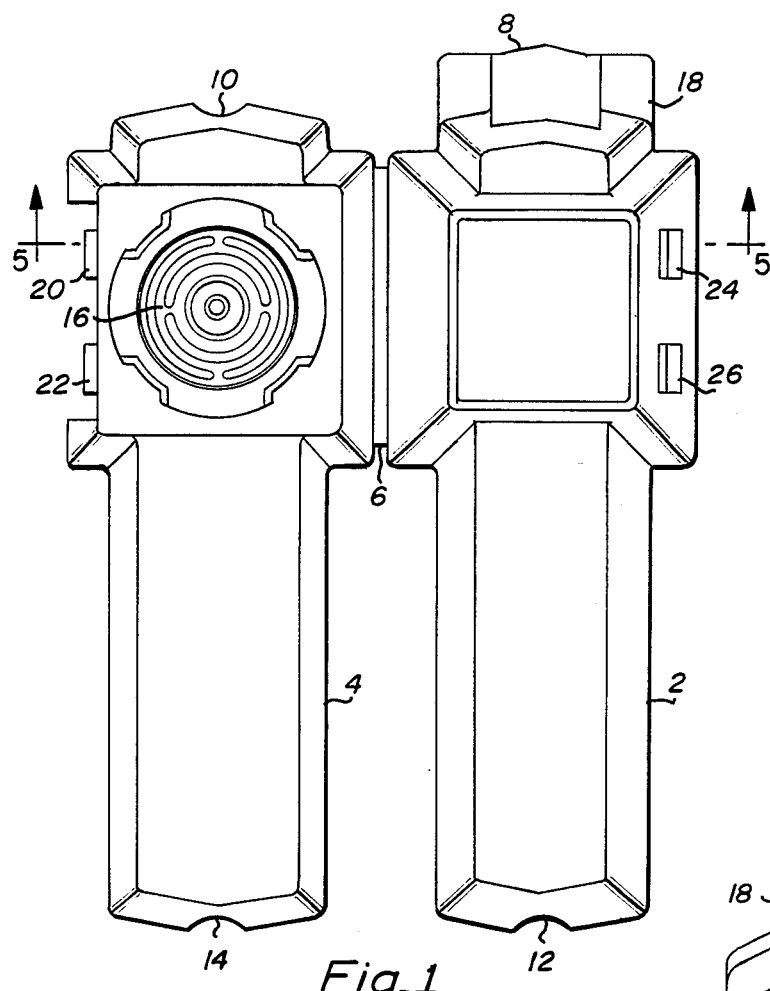
Fig_1
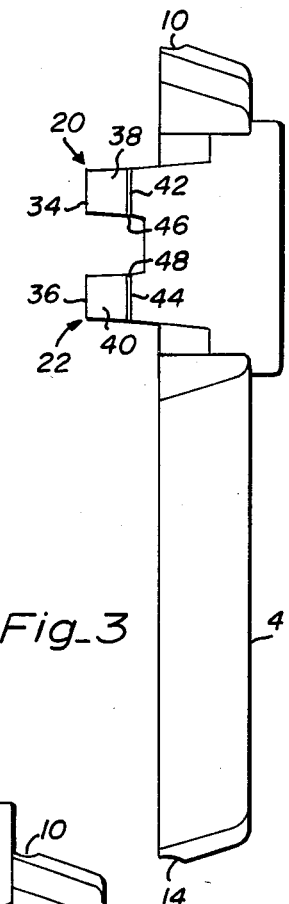
Fig_3
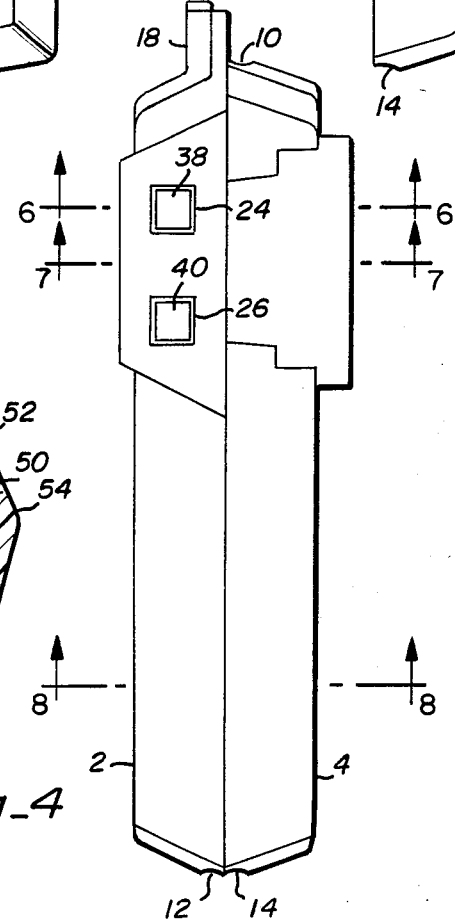
Fig_4
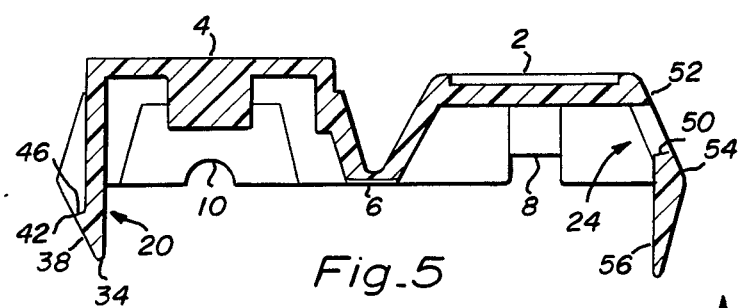
Fig_5

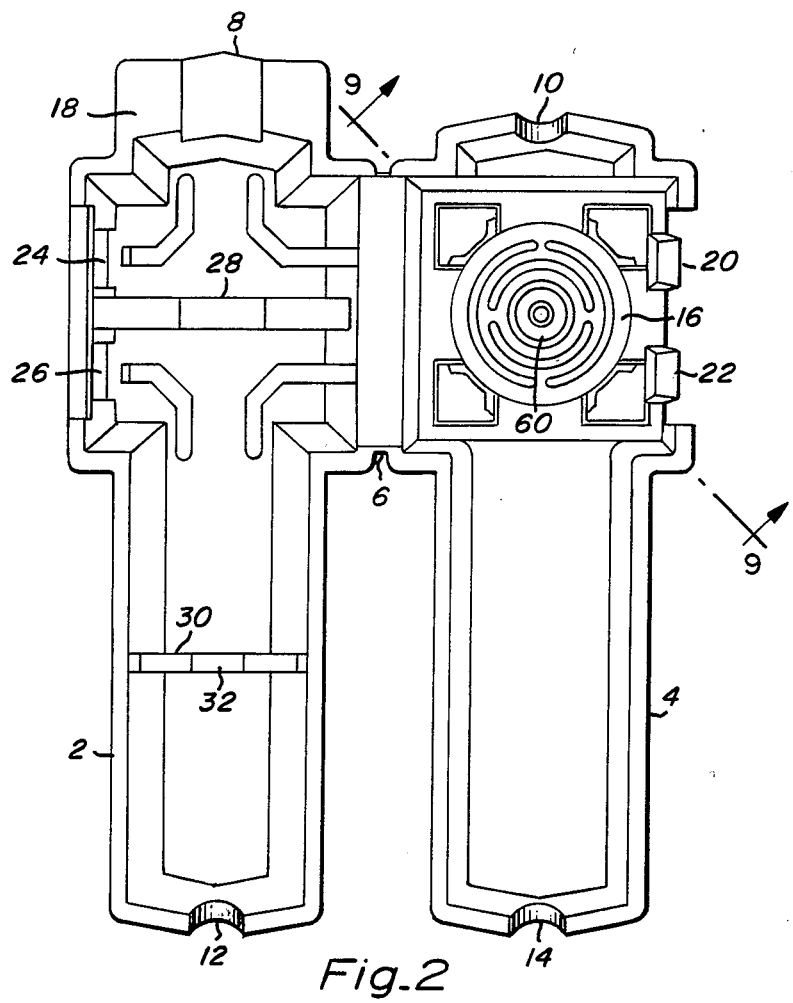
Fig_2
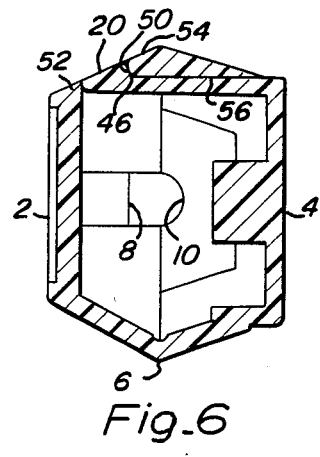
Fig_6
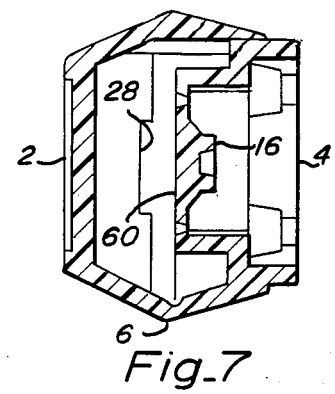
Fig_7
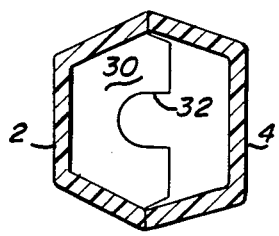
Fig_8
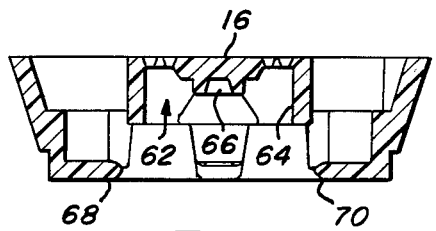
Fig_9
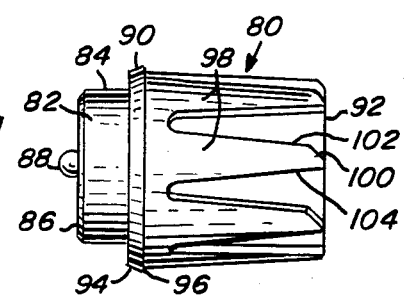
Fig_10

PINCH VALVE ASSEMBLY

FIELD OF THE INVENTION

This invention relates to an apparatus or administering parenteral solutions to medical patients. In particular, this application is directed to an improved apparatus for delivering solutions at precise rates using a pinch valve flow control assembly.

BACKGROUND OF THE INVENTION

DESCRIPTION OF THE PRIOR ART

Infusion delivery systems for delivering liquid to a patient from more than one solution source have been previously known. The most common systems use gravity flow and manually adjustable tubing clamps or pinch valves. They may employ a variety of valves and junctions to control flow at the desired rate and sequence. Examples of such systems are described in U.S. Pat. Nos. 3,886,937; 4,034,754; 4,114,617; 4,219,022; 4,223,695; 4,236,515; 4,237,879; 4,237,880; 4,250,879; 4,252,116; 4,256,104; 4,256,105; and 4,258,712.

Automatic flow control systems relying on a drop counter which measures the frequency of drop fall through a drip chamber have been previously known. In general, a light beam from a lamp to a light detector is positioned so that it is interrupted by drops falling through a drip chamber. The frequency of the breaking of the light beam and/or the time lapse between drops breaking the light beam are directly proportional to the flow rate and are used to determine adjustments to be made to a flow control valve to change flow to the desired rate. Examples of systems comprising drop counters and control systems responsive thereto are described in U.S. Pat. Nos. 3,163,179; 3,601,124; 3,886,937; 4,038,982; 4,314,567.

The prior art pinch valve systems do not provide the precision and reliability needed to control flow rates.

SUMMARY AND OBJECTS OF THE INVENTION

It is an object of this invention to provide an inexpensive, disposable, pinch valve assembly suitable for use with automatic control systems capable of providing a highly precise flow rate of fluid to a patient.

The disposable pinch valve assembly of this invention is designed for use with parenteral solution delivery systems employing flexible tubing. It comprises a tubing receptor housing having a mutually engagable tubing support front section and back section engagable therewith. The front section includes a stationary pressure plate against which tubing can be pressed. The back section includes an movable pressure plate for pressing tubing against the stationary pressure plate to reduce the cross-sectional area of the flow passageway of the tubing. The movable plate is displaced in response to movement of a motor-driven actuator.

In one embodiment of the invention, the front section and back section are hingedly connected along one edge and have mutually engaging, irreversible connecting means on the opposite edge thereof. The movable plate means comprises a circular plate connected by flexible web connectors to an outer rim defined by the back section. The back section has a threaded recess for engagingly receiving an actuating connector. The actuating connector has a motor drive connector at one end and a threaded cylindrical actuator at the opposite end for engaging the threaded recess.

BRIEF SUMMARY OF THE DRAWINGS

FIG. 1 is a frontal view of the disposable pinch valve housing of this invention in the open position.

FIG. 2 is a back view of the disposable pinch valve housing of this invention in the open position.

FIG. 3 is a side view of the disposable pinch valve housing of this invention in the open position.

FIG. 4 is a side view of the disposable pinch valve housing of this invention in the closed position.

FIG. 5 is a cross-sectional view taken along the line 5—5 in the representation of the open pinch valve housing shown in FIG. 1.

FIG. 6 is a cross-sectional view taken along the line 6—6 in the representation of the closed pinch valve housing shown in FIG. 4.

FIG. 7 is a cross-sectional view taken along the line 7—7 in the representation of the closed pinch valve housing shown in FIG. 4.

FIG. 8 is a cross-sectional view taken along the line 8—8 in the representation of the closed pinch valve housing shown in FIG. 4.

FIG. 9 is a cross-sectional view taken along the line 9—9 in the representation of the pinch valve housing shown in FIG. 2.

FIG. 10 is a side view of the actuating connector of this invention.

DETAILED DESCRIPTION OF THE INVENTION

Figure 14:
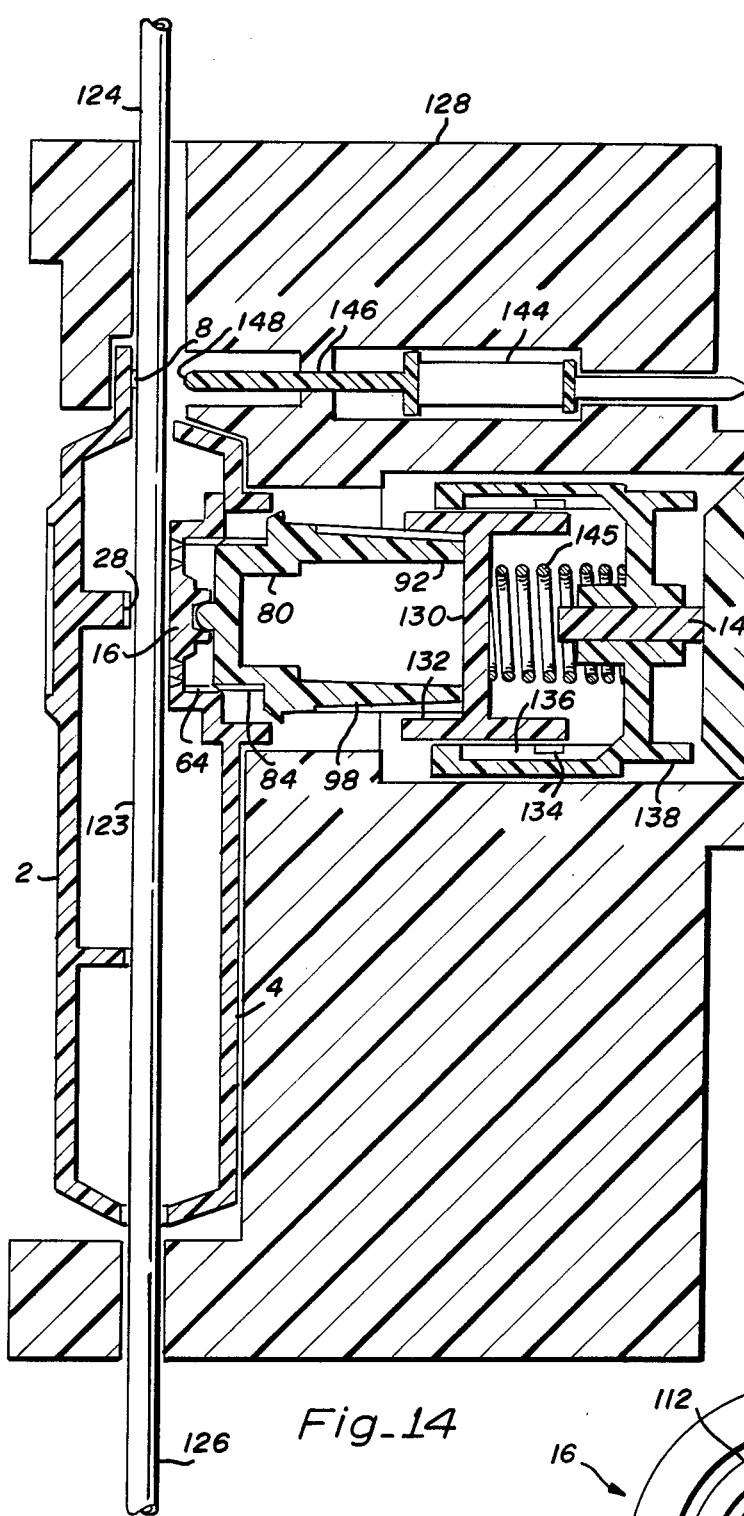
FIG. 14 is a cross-sectional view of the disposable pinch valve assembly of this invention.

Referring to FIGS. 1 and 2, the frontal and back views of the pinch valve housing in the open position are shown. The tubing receptacle housing comprises a front section 2 and a back section 4 joined by integral connecting hinge 6 along the common edge thereof. The tubing passes into the housing through the upper passageway defined by the stationary pressure plate 8 of the front section and upper tubing passageway 10 in the back section and exits between the lower passageway defined by the lower tubing passageway 12 in the front section and the lower tubing passageway 14 in the back section. The movable pressure plate 16 and connector webbing associated therewith are described in greater detail hereinafter with respect to FIGS. 11, 12 and 13. The latch projection 18 engages a retention latch described hereinafter with respect to FIG. 14. Snap connector means hold the front and back housing sections in irreversible engagement once they are closed into the mutually engaging position. The snap connector means comprises latch projections 20 and 22 of the receptor section and latch receptors 24 and 26 in the support section.

Referring to FIG. 2, the stationary pressure plate 28 has a flat surface transverse to the axis of the tubing passageways 8 and 12. The pressure plate 28 constitutes a surface against which tubing can be pressed. The movable pressure plate 16 when advanced against tubing held between it and the stationary pressure plate 28 pinches the tubing, reducing the cross-sectional area of the passageway therethrough. The rate of liquid flow through the tubing can be controlled by regulating the distance between the movable and stationary pressure plates. The tubing support webbing 30 having a recess 32 which positions the tubing exactly between the passageways 8 and 12 and between the pressure plates 16 and 28 when the housing is closed around a tubing section.

FIG. 3 is a side view of the disposable pinch valve housing of this invention in the open position. The latch projections 20 and 22 have respective leading tips 34 and 36, including leading surfaces 38 and 40 which taper to projecting ribs or teeth 42 and 44 described in detail with regard to FIG. 5 hereinafter. The trailing surfaces 46 and 48 are critical for achieving an irreversible engagement of the housing in the closed position.

FIG. 4 is a side view of the disposable pinch valve assembly of this invention in the closed position. In this view the leading surfaces 38 and 40 of the latch projections 18 and 20 can be seen in the engaged position in the latch receptors 24 and 26.

FIG. 5 is a cross-sectional view taken along the line 5—5 in FIG. 2. Latch projections 20 can be seen to have a leading tip 34 and a rib or tooth 42 formed by the leading surface 38. This surface leads from the tip 34 to the edge of the tooth. The trailing surface 46 of the projection forms a sharp and preferably an acute angle with respect to the leading surface 38. The latch receptor 24 comprises an opening, the forward edge of which constitutes a stop 50.

FIG. 6 is a cross-sectional view of the disposable pinch valve assembly of this invention in the closed position taken along the line 6—6 in FIG. 4. The latch projection 20 is made of flexible plastic and is deflected during closure to pass by the housing surface 56. The projection 20 then resiliently returns to its unflexed orientation to snap into the opening of the latch receptor 24 (FIG. 5). Efforts to separate the housing are made difficult because the leading surface 38 of the latch projection 20 is flush with adjacent surfaces 52 and 54 of the front housing section 2. Furthermore, opening movement is prevented by the opposed surfaces of the trailing surface 46 and the stop 50. The hinge 6 provides a hinge binding action, full closure of the sections placing the hinge under tension. If closure is incomplete, this tension forces the front and back sections into a conspicuously open position, prompting the attendant to repeat the closure step until a complete closure is effected.

A critical function of this latch system is to prevent removal of this disposable pinch valve assembly from tubing once it is engaged in a fully functional way. This is an inexpensive disposable unit, and repeated use would risk loss of accurate control of flow rates. Therefore, it is critical that the latching mechanism prevent reuse.

FIG. 7 is a cross-sectional view of the disposable pinch valve assembly of this invention in the closed position taken along the line 7—7 in FIG. 4. The relative positions of the stationary pressure plate surface 28 and the movable pressure plate surface 60 can be seen. Tubing placed between the surfaces 28 and 60 can be squeezed by moving the movable pressure plate 16 in an axial direction towards the stationary pressure plate 28.

FIG. 8 is a cross-sectional view of the disposable pinch valve assembly of this invention in a closed position taken along line 8—8 in FIG. 4. In this drawing, the webbing 30 and tubing recess 32 is shown. This supports the tubing in a secure manner when engaging the two sections of the housing to maintain the tubing in a proper position between the movable pressure plate surface 60 and stationary pressure plate surface 28 until closure is complete.

FIG. 9 is a cross-sectional view of the pinch valve housing taken along the line 9—9 in FIG. 2. The actuating connector receptor recess 62 is a cylindrical recess having female threads 64. A recess 66 which engages the actuating connector after assembly is axially positioned in the center of the movable pressure plate 16. The retention snaps 68 and 70 function to retain the actuating connector means in position after assembly as described hereinafter with respect to FIGS. 11, 12 and 13.

FIG. 10 is a side view of the actuating connector 80. The actuating end of the actuating connector comprises a cylindrical connecting end 82 having male threads 84 and a leading surface 86 with an axially central projection 88. Annular flange 90 intermediate the connecting end 82 and the cylindrical motor drive connecting end 92 extends outwardly. The sloped leading surface 94 forms an acute angle with the trailing surface 96 for latching engagement with snap means 68 and 70 as shown in FIG. 9.

The motor connecting end of the actuating connector 80 comprises a cylinder which is axially aligned with the connector end 82. A plurality of splines 98 are formed in the outer surface of the cylinder surface. Each spline has a tip 100 which forms an obtuse angle with the trailing edge 102. The tip 100 forms an acute angle with the leading edge 104. The splines 98 join at their base in an acute angle. This configuration permits easy engagement with the female splines of the motor coupler shown in FIG. 14.

Figure 11:
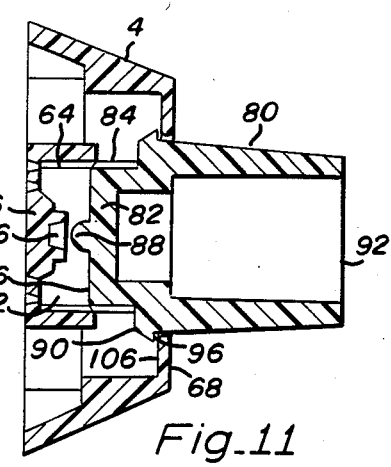
FIG. 11 is a cross-sectional view showing the actuating connector assembled with the pinch valve housing in the initial assembly position.

FIG. 11 is a cross-sectional view of the assembled back housing section 4 and the actuating connector 80. In this view, the connecting end 82 of the actuating connector 80 engaging the receptor recess 62. The projection 88 is positioned to engage the recess 66 in the movable pressure plate 16. The trailing surface 96 of the flange 90 engages the corresponding stop surface 106 of the retention snap 68 to retain the actuating connector securely in place after assembly. The distance between the leading face 86 and the trailing surface 96 of the actuating connector is insufficient to force the male threads 84 into engagement with the female threads 64. The actuating connector 80 can rotate freely after being assembled with the back housing section 4 without causing a premature engagement of the male threads 84 and female threads 64. This protects the movable pressure plate 16 and webbed connecting structure from stress and damage prior to actual use.

Figure 12:
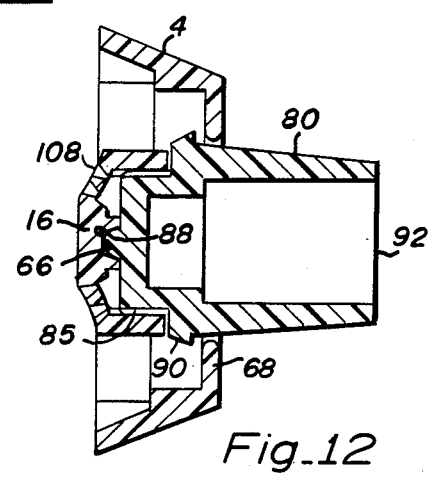
FIG. 12 is a cross-sectional view showing the actuating connector assembled with the back housing section after actuating movement of the connector.

FIG. 12 is a cross-sectional view showing the actuator connector assembled with the back housing section after actuating movement of the connector. The forward actuating movement of the actuating connector 80 causes engagement 85 of the male threads 84 with the female threads 64 shown in FIG. 4. Rotation of the actuating connector 80 about its axis (in response to motor activation) causes advancement of the projection 88 and engagement with recess 66. Continued advancement displaces movable pressure plate 16 in an axial direction. Reverse rotation removes pressure on recess 66 permitting the movable pressure plate 16 to return toward its relaxed position, the webbing 108 providing the resiliency.

Figure 13:
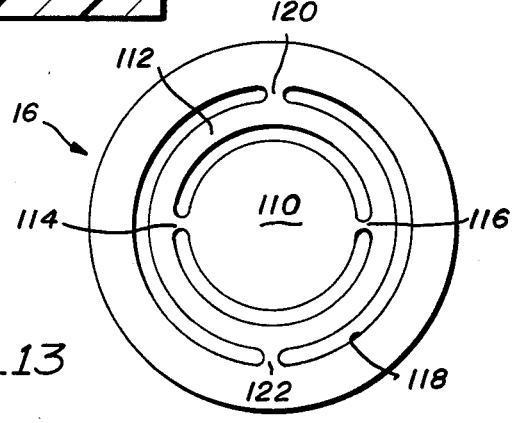
FIG. 13 is a representation of the back view of the movable plate showing the web construction.

FIG. 13 is a detailed view of the movable pressure plate. The movable pressure plate 16 comprises the circular central plate 110. The circular ring 112 is connected to the central plate 110 by webs 114 and 116. The circular ring 112 is attached to the outer rim 118 by means of webs 120 and 122. The webbing is constructed of flexible, resilient organic polymers and provides an elastic, flexible movement of the central plate 110 in an axial direction both toward and away from the stationary pressure plate 28.

FIG. 14 is a cross-sectional view of the fully assembled disposable pinch valve of this invention. The front section 2 and back section 4 of the pinch valve are closed on a suitably positioned flexible tubing 123, the tubing end 124 leading from a solution supply and the tubing end 126 leading to the patient. The actuating connector 80 is assembled with the back section 4 of the pinch valve housing as shown in FIG. 11. The closed housing is then positioned in a recess in the motor housing 128.

The motor connector end 92 of the actuating connector 80 fits into the axially movable motor coupler 130, the splines 98 meshing with female projections 132 in a sliding engagement. The motor coupler 130 has male projections 134 which slide in grooves 136 in the coupling wheel 138. The coupling wheel is mounted on the drive shaft 140 of motor 142. Motor 142 can be any type of motor which can be controlled to move in preselected increments.

The spring 145 pushes the motor coupler and the actuating connector axially forward, the initial rotation of the coupling wheel 138 effects a threaded engagement of the threads 80 of the actuating connector 80 and threads 64 of the receptor recess. Continued rotation of wheel 138 advances the projection 88 and the movable pressure plate 16 toward the stationary pressure plate 28, reducing the cross-sectional area of the tubing passageway therebetween. Reverse rotation of wheel 138 reverses this axial movement in the direction away from the tubing, permitting the resilient tubing to return toward its relaxed configuration and increasing the cross-sectional area of the tubing passageway.

An additional safety feature is provided by the latch projection 18 on the front housing section 2. The rear surface 8 thereof functions as a stationary pressure plate. Actuation of the solenoid 144 drives the projection 146 against the tubing, the end 148 thereof tightly pinching the tubing against the surface 8. This completely closes the tubing, terminating fluid flow therethrough. The solenoid 144 can be automatically actuated in a manner known per se in the art in response to a system malfunction presenting risk to the patient.

The invention claimed is:

1. A disposable pinch valve assembly for a parenteral solution delivery system comprising a tubing receptor housing having mutually engagable front and back sections, the front section and back section thereof being hingedly connected along one edge and having an irreversible connecting means on the opposite edge thereof, the front section including a stationary pressure plate means against which tubing can be pressed, the back section including a movable pressure plate means for pressing tubing against said stationary pressure plate to reduce the cross-sectional area of the flow passageway of the tubing in response to axial displacement by a motor-driven actuator, wherein the irreversible connection means comprises a snap connection with a projection latch member and a receptor latch member, the projection latch member having a tooth defined by a sloped surface leading from the tip of the projecting latch member and a following surface which forms an acute angle with respect to the sloped surface, and the receptor latch member having a passageway for receiving the projecting latch member and a stop means which, by abutting the following surface of the projection latch member in latching engagement prevents withdrawal of the projecting latch member from the receptor latch member.

2. A disposable pinch valve for a parenteral solution delivery system comprising a tubing receptor housing having mutually engagable front and back sections, the front section including a stationary pressure plate means against which tubing can be pressed, the back section including an outer rim and a movable pressure plate means for pressing tubing against said stationary pressure plate to reduce the cross-sectional area of the flow passageway of the tubing in response to axial displacement by a motor-driven actuator, the movable pressure plate means including a circular central plate connected to the outer rim by flexible radial web members.

3. The disposable pinch valve assembly of claim 2 wherein the web connector means comprises a flexible circular ring connected to the central plate and to the outer rim by the radial web members.

4. The disposable pinch valve assembly of claim 3 wherein the web members connecting the circular ring with the central plate are angularly displaced with respect to the web members connecting the circular ring with the outer rim.

5. A disposable pinch valve for a parenteral solution delivery system comprising a tubing receptor housing having mutually engagable front and back sections, the front section including a stationary pressure plate means against which tubing can be pressed, the back section including a movable pressure plate means for pressing tubing against said stationary pressure plate to reduce the cross-sectional area of the flow passageway of the tubing in response to axial displacement by a motor-driven actuator and an actuator connector retention means, the movable pressure plate defining a threaded recess for engagingly receiving a threaded actuator connector means, and threaded actuator connector means having a connecting end with a threaded male member for engaging the threaded recess and a motor drive end for engaging a motor drive means, the connecting end having an annular flange engaging the actuator connector retention means.

6. The disposable pinch valve assembly of claim 5 in combination with a motor coupler having female projections, wherein the actuator connector has a plurality of spline means in the outer cylindrical surface thereof for engaging the female projections in sliding engagement.

7. A disposable pinch valve for a parenteral solution delivery system in combination with a motor housing comprising a tubing receptor housing having mutually engagable front and back sections, the front section including a first stationary pressure plate means against which tubing can be pressed, the back section including a movable pressure plate means for pressing tubing against said first stationary pressure plate to reduce the cross-sectional area of the flow passageway of the tubing in response to axial displacement by a motor-driven actuator, the front section having a latch projection means for engaging a retaining means in the motor housing, the latch projection means having a second stationary pressure plate surface against which tubing can be pinched to terminate fluid flow therethrough, the motor housing having a movable means for pressing tubing against the secondary pressure plate surface in response to a system malfunction.

* * * * *